US010067206B2

(12) United States Patent
Takayama et al.

(10) Patent No.: US 10,067,206 B2
(45) Date of Patent: Sep. 4, 2018

(54) MEDICAL IMAGE DIAGNOSIS APPARATUS AND PET-MRI APPARATUS

(71) Applicant: TOSHIBA MEDICAL SYSTEMS CORPORATION, Otawara-Shi (JP)

(72) Inventors: Takuzo Takayama, Utsunomiya (JP); Hitoshi Yamagata, Otawara (JP); Kazuya Okamoto, Saitama (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 1012 days.

(21) Appl. No.: 14/450,697

(22) Filed: Aug. 4, 2014

(65) Prior Publication Data
US 2014/0343400 A1 Nov. 20, 2014

Related U.S. Application Data

(63) Continuation of application No. PCT/JP2013/062138, filed on Apr. 24, 2013.

(30) Foreign Application Priority Data

Apr. 24, 2012 (JP) .................. 2012-099023
Apr. 24, 2013 (JP) .................. 2013-091808

(51) Int. Cl.
A61B 5/055 (2006.01)
A61B 6/00 (2006.01)
(Continued)

(52) U.S. Cl.
CPC .......... G01R 33/481 (2013.01); A61B 5/0035 (2013.01); A61B 5/0037 (2013.01);
(Continued)

(58) Field of Classification Search
CPC ..... A61B 5/0035; A61B 5/0037; A61B 5/055; A61B 6/037; A61B 6/0457; A61B 6/4258;
(Continued)

(56) References Cited

U.S. PATENT DOCUMENTS 8,563,935 B2   10/2013 Teshigawara
2008/0146914 A1   6/2008 Polzin et al.
(Continued)

FOREIGN PATENT DOCUMENTS

JP   63-302830 A   12/1988
JP   2008-134205 A   6/2008
(Continued)

OTHER PUBLICATIONS

International Search Report dated Jun. 18, 2013 for PCT/JP2013/062138 filed on Apr. 24, 2013 with English Translation.
(Continued)

Primary Examiner — Ruth S Smith
(74) Attorney, Agent, or Firm — Oblon, McClelland, Maier & Neustadt, L.L.P.

(57) ABSTRACT

A medical image diagnosis apparatus according to an embodiment includes: a first image taking unit, a second image taking unit, a position specifying unit, and a moving controlling unit. The first image taking unit performs an image taking process by implementing PET while using a first PET detector and a second PET detector. The position specifying unit specifies positions of the first PET detector and the second PET detector, on the basis of a medical image taken by the second image taking unit. The moving controlling unit controls moving of the first PET detector and the second PET detector in accordance with the specified positions. The first image taking unit and the second image taking unit each perform the image taking process after the
(Continued)

first PET detector and the second PET detector have been moved.

16 Claims, 9 Drawing Sheets

(51) Int. Cl.
G01R 33/48 (2006.01)
A61B 6/03 (2006.01)
A61B 5/00 (2006.01)
G01T 1/16 (2006.01)
G01T 1/29 (2006.01)
A61B 6/04 (2006.01)

(52) U.S. Cl.
CPC .............. *A61B 5/055* (2013.01); *A61B 6/037* (2013.01); *A61B 6/0457* (2013.01); *A61B 6/4258* (2013.01); *A61B 6/4417* (2013.01); *A61B 6/5235* (2013.01); *A61B 6/5247* (2013.01); *A61B 6/547* (2013.01); *G01T 1/1603* (2013.01); *G01T 1/2985* (2013.01); A61B 6/4266 (2013.01)

(58) Field of Classification Search
CPC ... A61B 6/4266; A61B 6/4417; A61B 6/5235; A61B 6/5247; A61B 6/547; G01R 33/481; G01T 1/1603; G01T 1/2985
See application file for complete search history.

(56) References Cited

U.S. PATENT DOCUMENTS

| | | |
|---|---|---|
| 2008/0243759 A1 | 10/2008 | Martin et al. |
| 2010/0033186 A1 | 2/2010 | Overweg et al. |
| 2010/0290584 A1 | 11/2010 | Vesel et al. |
| 2011/0224534 A1 | 9/2011 | Yamaya et al. |
| 2011/0299655 A1 | 12/2011 | Takayama |
| 2012/0150017 A1 | 6/2012 | Yamaya et al. |
| 2012/0161014 A1 | 6/2012 | Yamaya et al. |
| 2013/0234710 A1 | 9/2013 | Kanno et al. |
| 2013/0241555 A1 | 9/2013 | Obata et al. |
| 2013/0296689 A1 | 11/2013 | Okamoto et al. |
| 2013/0324836 A1 | 12/2013 | Yamaya et al. |

FOREIGN PATENT DOCUMENTS

| | | |
|---|---|---|
| JP | 2008-229343 A | 10/2008 |
| JP | 2010-523191 A | 7/2010 |
| JP | 2011-502567 A | 1/2011 |
| JP | 2012-13680 A | 1/2012 |
| JP | 2012-73243 | 4/2012 |
| WO | 2010/103644 A1 | 9/2010 |
| WO | 2010/103645 A1 | 9/2010 |

OTHER PUBLICATIONS

International Written Opinion dated Jun. 18, 2013 for PCT/JP2013/062138 filed on Apr. 24, 2013.
U.S. Appl. No. 14/522,024, filed Oct. 23, 2014, Okamoto, et al.

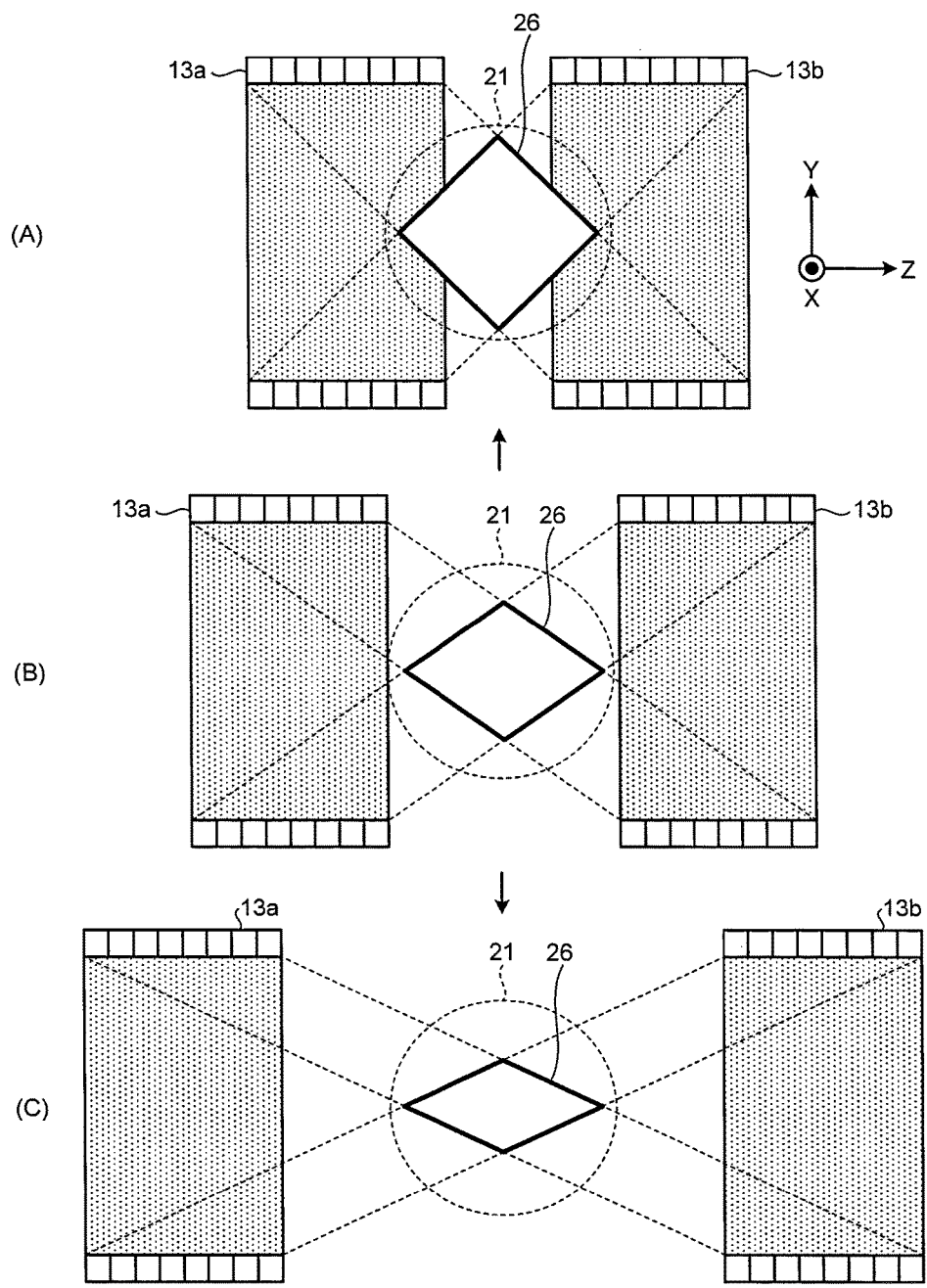

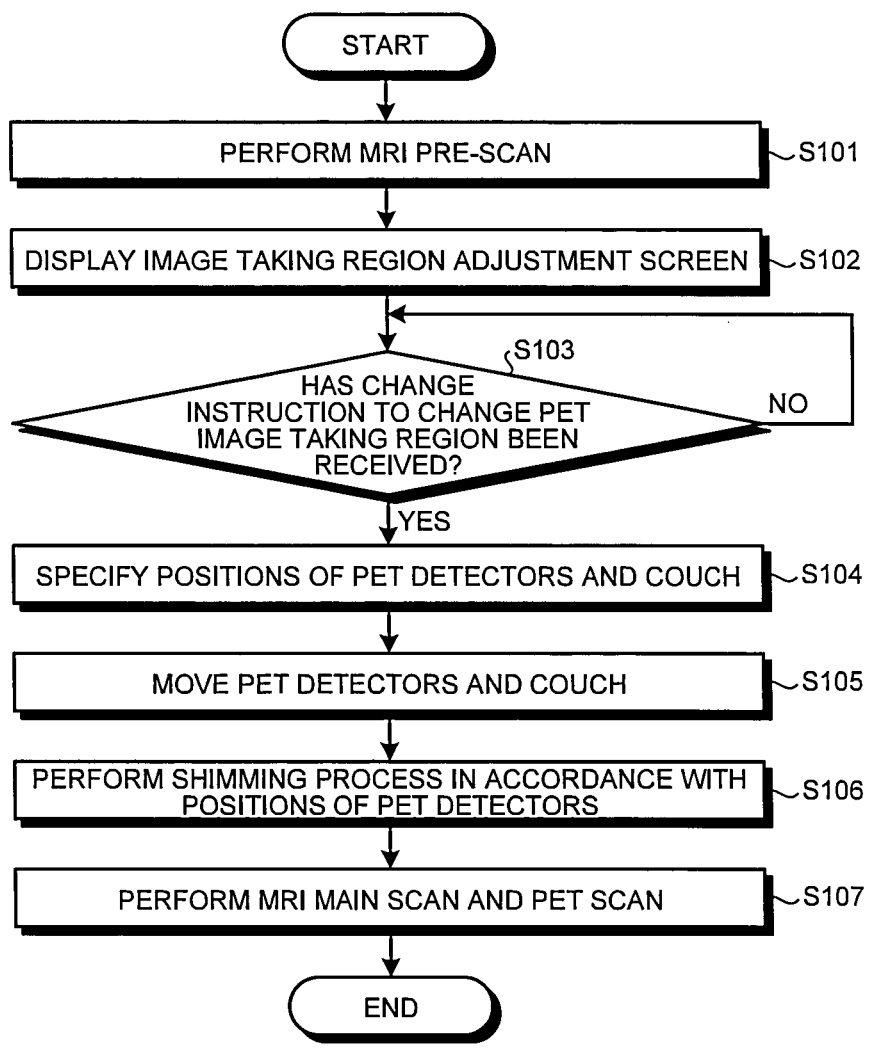

MEDICAL IMAGE DIAGNOSIS APPARATUS AND PET-MRI APPARATUS

CROSS-REFERENCE TO RELATED APPLICATIONS

This application is a continuation of PCT international application Ser. No. PCT/JP2013/062138 filed on Apr. 24, 2013 which designates the United States, incorporated herein by reference, and which claims the benefit of priority from Japanese Patent Application No. 2012-099023 filed on Apr. 24, 2012; and Japanese Patent Application No. 2013-091808, filed on Apr. 24, 2013, the entire contents of which are incorporated herein by reference.

FIELD

Embodiments described herein relate generally to a medical image diagnosis apparatus and a PET-MRI apparatus.

BACKGROUND

Conventionally, "PET-CT apparatuses" in each of which a Positron Emission Tomography apparatus (hereinafter, a "PET apparatus") and an X-ray Computed Tomography (CT) apparatus are combined together have been in practical use. Further, in recent years, "PET-MRI apparatuses" in each of which a PET apparatus and a Magnetic Resonance Imaging apparatus (hereinafter, an "MRI apparatus") are combined together are also expected to be in practical use. For example, PET-MRI apparatuses are expected to be in practical use for an early diagnosis of Alzheimer's disease.

BRIEF DESCRIPTION OF THE DRAWINGS

FIG. 5 is a drawing for explaining changes in the effective fields of vision of PET and MRI according to the present embodiment.

FIG. 6 is a flowchart of a processing procedure according to the present embodiment.

DETAILED DESCRIPTION

A medical image diagnosis apparatus according to an embodiment includes: a first image taking unit, a second image taking unit, a position specifying unit, and a moving controlling unit. The first image taking unit performs an image taking process by implementing PET while using a first PET detector and a second PET detector that are each a PET detector configured to detect annihilation radiation emitted from a positron emission nuclide and that are provided so that an interval therebetween is adjustable. The second image taking unit performs an image taking process by implementing an image taking method different from that of the first image taking unit. The position specifying unit specifies positions of the first PET detector and the second PET detector, on the basis of a medical image taken by the second image taking unit. The moving controlling unit controls moving of the first PET detector and the second PET detector in accordance with the specified positions. The first image taking unit and the second image taking unit each perform the image taking process after the first PET detector and the second PET detector have been moved.

In the following sections, exemplary embodiments of a PET-MRI apparatus will be explained in detail, with reference to the accompanying drawings.

Figure 1:
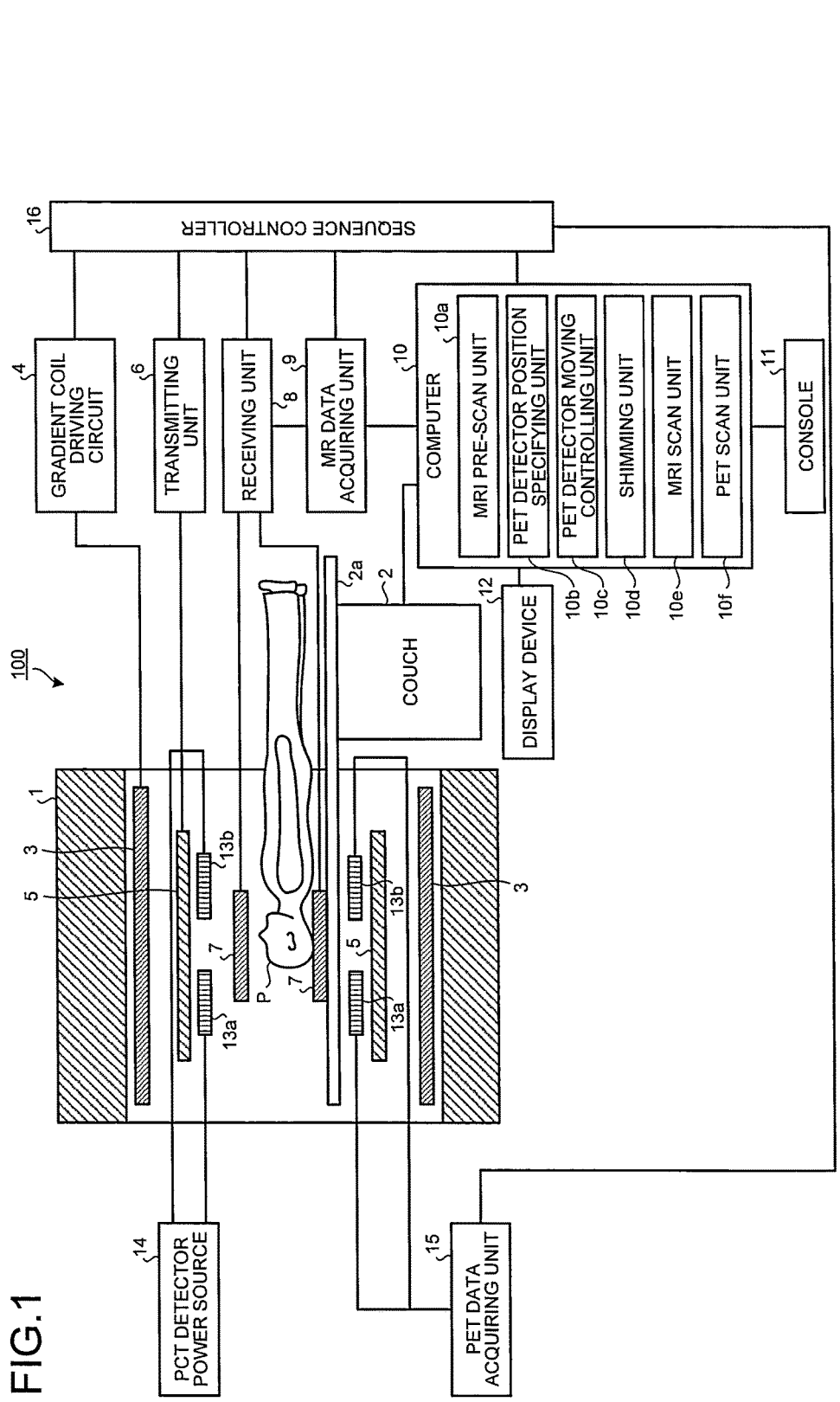
FIG. 1 is a diagram of a PET-MRI apparatus according to an embodiment.

FIG. 1 is a diagram of a PET-MRI apparatus 100 according to an embodiment. As shown in FIG. 1, the PET-MRI apparatus 100 includes a magnetostatic field magnet 1, a couch 2, a gradient coil 3, a gradient coil driving circuit 4, a transmission-purpose radio frequency coil 5, a transmitting unit 6, a reception-purpose radio frequency coil 7, a receiving unit 8, an Magnetic Resonance (MR) data acquiring unit 9, a computer 10, a console 11, a display device 12, PET detectors 13a and 13b, a PET detector power source 14, a PET data acquiring unit 15, and a sequence controller 16.

The magnetostatic field magnet 1 is configured to generate a magnetostatic field in the space on the inside of a bore. The bore is a structure formed in the shape of a substantially circular cylinder and stores therein the magnetostatic field magnet 1, the gradient coil 3, and the like. The couch 2 includes a couchtop 2a on which an examined subject (hereinafter, a "patient") P is placed. The patient P is moved into the magnetostatic field, by moving the couchtop 2a into the bore.

The gradient coil 3 is configured to apply gradient magnetic fields Gx, Gy, and Gz, of which the magnetic intensities, which are in the same direction as the magnetostatic field, change substantially linearly with respect to the distances from the center of the magnetic field along the X-, Y-, and Z-directions, respectively. The gradient coil 3 is formed in the shape of a substantially circular cylinder and is disposed on the inner circumferential side of the magnetostatic field magnet 1. The gradient coil driving circuit 4 is configured to drive the gradient coil 3, under control of the sequence controller 16.

On the basis of a radio frequency pulse transmitted from the transmitting unit 6, the transmission-purpose radio frequency coil 5 is configured to apply a radio frequency magnetic field to the patient P placed in the magnetostatic field. The transmission-purpose radio frequency coil 5 is formed in the shape of a substantially circular cylinder and is disposed on the inner circumferential side of the gradient coil 3. The transmitting unit 6 is configured to transmit the radio frequency pulse to the transmission-purpose radio frequency coil 5, under control of the sequence controller 16.

The reception-purpose radio frequency coil 7 is configured to detect magnetic resonance signals emitted from the patient P as a result of the applications of the radio frequency magnetic field and the gradient magnetic fields. For example, the reception-purpose radio frequency coil 7 is configured with a surface coil disposed on the body surface of the patient P in accordance with the image taking target site. The receiving unit 8 is configured to receive the magnetic resonance signals detected by the reception-purpose radio frequency coil 7, under control of the sequence controller 16. Further, the receiving unit 8 sends the received magnetic resonance signals to the MR data acquiring unit 9.

The MR data acquiring unit 9 is configured to acquire the magnetic resonance signals sent from the receiving unit 8, under control of the sequence controller 16. Further, the MR data acquiring unit 9 generates MR data by performing an amplifying process and a wave-detecting process on the acquired magnetic resonance signals and further performing an analog/digital (A/D) conversion thereon. The MR data acquiring unit 9 then sends the generated MR data to the computer 10.

The PET detectors 13a and 13b are configured to detect annihilation radiation (hereinafter, "gamma rays") emitted from a positron emission nuclide administered to the patient P, as count information. Further, the PET detectors 13a and 13b sends the detected count information to the PET data acquiring unit 15. Each of the PET detectors 13a and 13b is formed in a ring shape and is disposed on the inner circumferential side of the transmission-purpose radio frequency coil 5. For example, each of the PET detectors 13a and 13b is configured by arranging a detector module that includes a scintillator and an optical detector to be in a ring form. In this situation, the scintillator is, for example, Lutetium Yttrium Oxyorthosilicate (LYSO), Lutetium Oxyorthosilicate (LSO), or Lutetium Gadolinium Oxyorthosilicate (LGSO). The optical detector is, for example, a semiconductor detector such as an Avalanche Photodiode (APD) element or a Silicon Photomultiplier (SiPM), or a Photomultiplier Tube (PMT).

The PET detector power source 14 is configured to supply electric power used for driving the optical detectors to the PET detectors 13a and 13b. The PET data acquiring unit 15 is configured to acquire the count information sent from the PET detectors 13a and 13b, under control of the sequence controller 16. Further, by using the acquired count information, the PET data acquiring unit 15 generates coincidence list information as PET data, the coincidence list information indicating sets each made up of pieces of count information in which gamma rays are detected substantially at the same time. The PET data acquiring unit 15 then sends the generated PET data to the computer 10.

The sequence controller 16 is configured to control the functional units described above, on the basis of various types of image taking sequences that are executed during image taking processes.

Figure 2:
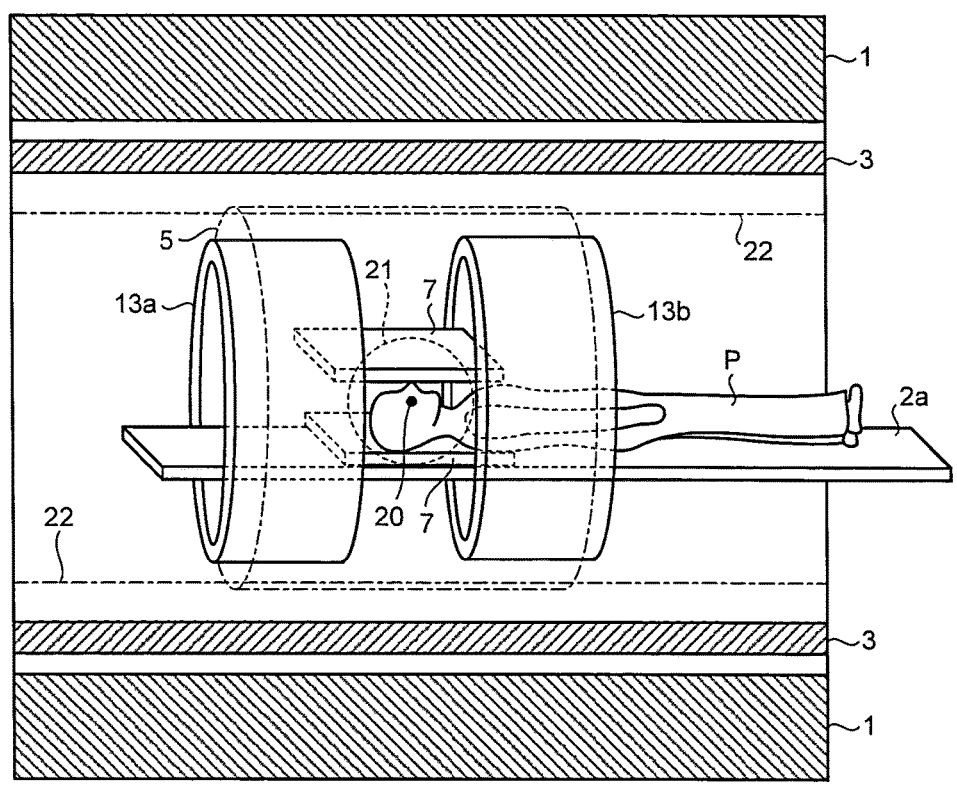
FIG. 2 is a drawing for explaining positional arrangements of functional units in the surroundings of PET detectors according to the present embodiment.
Figure 3:
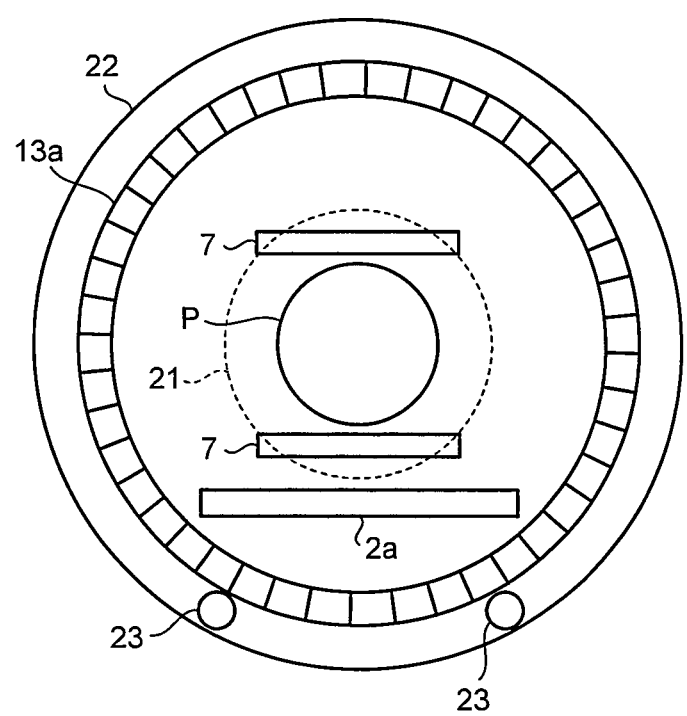
FIG. 3 is another drawing for explaining positional arrangements of functional units in the surroundings of the PET detectors according to the present embodiment.

FIGS. 2 and 3 are drawings for explaining positional arrangements of functional units in the surroundings of the PET detectors 13a and 13b according to the present embodiment. In FIG. 2, a point 20 indicates the magnetic-field center of the magnetostatic field. Further, in FIG. 2, a region 21 in a substantially spherical shape marked with a dotted line represents an effective field of vision of MRI. Further, in FIG. 2, a dashed line 22 represents the inner wall of the bore.

As illustrated in FIG. 2, according to the present embodiment, the PET detectors 13a and 13b are disposed on the inner circumferential side of the bore. Further, the PET detector 13a and the PET detector 13b are positioned so as to have an interval therebetween in the axial direction of the bore, while the magnetic-field center 20 of the magnetostatic field generated by the magnetostatic field magnet 1 is interposed therebetween. In other words, according to the present embodiment, the PET detectors 13a and 13b are positioned so as to avoid a surrounding area of the magnetic-field center 20, which corresponds to the effective field of vision of MRI. As a result, it is possible to prevent the image quality of Magnetic Resonance (MR) images from being degraded by influences of the PET detectors.

Further, the PET-MRI apparatus 100 includes moving mechanisms configured to move the PET detectors 13a and 13b along the axial direction of the bore. FIG. 3 is another drawing for explaining positional arrangements of functional units, with a view of the inside of the bore through the opening on the side where the PET detector 13a is provided. For example, as illustrated in FIG. 3, a moving mechanism 23 is configured with two rails that are installed below the inner wall 22 of the bore. For example, the moving mechanism 23 is fitted to rail receiving parts that are formed as grooves on the outer circumferential surface of the PET detector 13a, so that the PET detector 13a is supported while being movable along the axial direction of the bore. Similarly, another moving mechanism 23 for moving the PET detector 13b is also installed on the side where the PET detector 13b is provided.

Each of the PET detectors 13a and 13b is detachable from the respective moving mechanism 23. It is therefore possible to move the PET detectors 13a and 13b in and out of the bore from either side of the openings of the bore. Because the PET detectors 13a and 13b are structured so as to be detachable in this manner, it is relatively easy to incorporate the PET detectors 13a and 13b into a conventional MRI apparatus, and it is thus possible to promote the PET detectors 13a and 13b to be widely used.

Figure 4A:
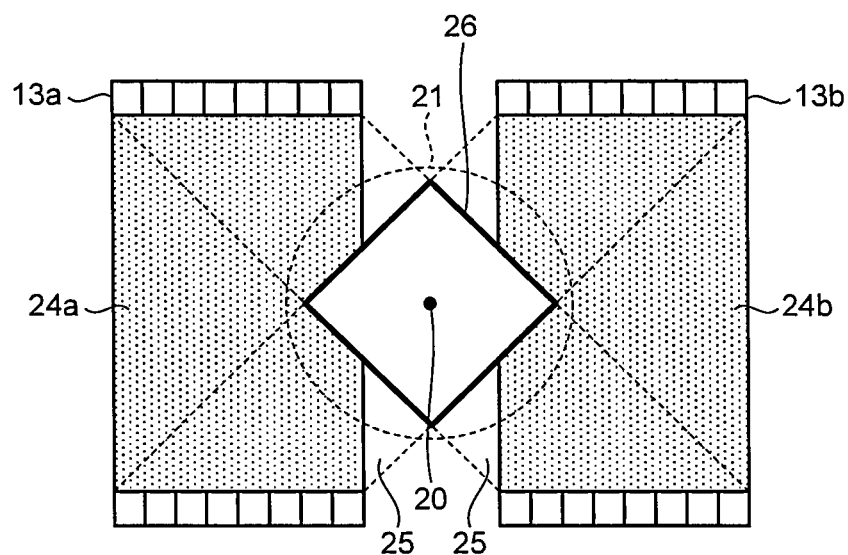
FIG. 4A is a drawing for explaining effective fields of vision of PET and MRI according to the present embodiment.
Figure 4B:
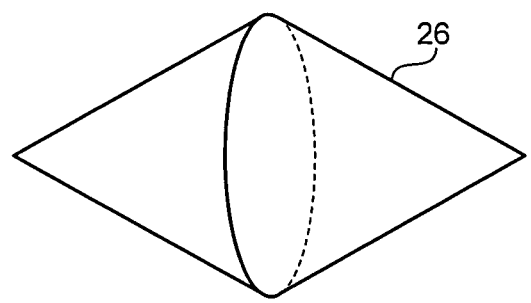
FIG. 4B is another drawing for explaining effective fields of vision of PET and MRI according to the present embodiment.

FIGS. 4A and 4B are drawings for explaining effective fields of vision of PET and MRI according to the present embodiment. An effective field of vision is a region in which it is possible to acquire data (of a region in which the image quality is to be guaranteed) that is effective as data to be an imaging target. Effective fields of vision of the PET-MRI apparatus 100 include: an "effective field of vision of PET" where it is possible to acquire data that is effective for a PET image; an "effective field of vision of MRI" where it is possible to acquire data that is effective for an MR image; and an "effective field of vision of PET-MRI" where it is possible to acquire data that is effective for both a PET image and an MR image.

First, generally speaking, as illustrated in FIG. 4A, an effective field of vision of MRI can be represented by the region 21 that has a substantially spherical shape centered on the magnetic-field center 20. In contrast, an effective field of vision of PET can be represented by a region 24a enclosed by the inner circumferential surface of the PET detector 13a and a region 24b enclosed by the inner circumferential surface of the PET detector 13b. In addition, a region 25 formed between the inner circumferential surface of the PET detector 13a and the inner circumferential surface of the PET detector 13b is also an effective field of vision of PET.

Accordingly, an effective field of vision of PET-MRI is represented by overlapping parts between the effective field of vision of PET and the effective field of vision of MRI, i.e., the parts that are in the effective field of vision of MRI 21 and that also overlap with the effective fields of vision of PET 24a, 24b, and 25. However, from among these overlapping parts, a region 26 that has a substantially rhomboid shape as illustrated in FIG. 4A will be used, in particular, as an effective field of vision of PET-MRI in the present embodiment, from the viewpoint of guaranteeing the image quality. As illustrated in FIG. 4B, the substantially rhomboid-shaped region 26 has a shape obtained by substantially putting the bottom faces of cones against each other. The effective field of vision of PET-MRI does not necessarily have to be the region 26 illustrated in FIG. 4A. In another example, it is acceptable to generally use the overlapping parts between the effective field of vision of PET and the effective field of vision of MRI as an effective field of vision of PET-MRI. Further, for example, the effective field of vision will be different depending on the sizes of the PET detectors 13a and 13b.

In this situation, the length of the effective field of vision of PET-MRI in the vertical direction can be changed along the axial direction of the bore by moving the PET detectors 13a and 13b. FIG. 5 is a drawing for explaining the changes in the effective fields of vision of PET and MRI according to the present embodiment. As mentioned above, the PET detectors 13a and 13b according to the present embodiment have the moving mechanisms, and it is therefore possible to adjust the interval therebetween. Starting with the state illustrated in FIG. 5(B), for example, by moving the PET detectors 13a and 13b, it is possible to reduce the interval between the PET detector 13a and the PET detector 13b, as illustrated in FIG. 5(A). As another example, it is possible to enlarge the interval between the PET detector 13a and the PET detector 13b, as illustrated in FIG. 5(C).

When the effective field of vision of PET-MRI 26 illustrated in FIG. 5(B) is compared with the effective field of vision of PET-MRI 26 illustrated in FIG. 5(A), it is observed that, although the dimension along the axial direction of the bore (i.e., the Z-axis direction) does not change, the dimension in the Y-axis direction is larger in the example illustrated in FIG. 5(A) where the interval between the PET detector 13a and the PET detector 13b is smaller. Further, as illustrated in FIG. 4(B), the effective field of vision of PET-MRI 26 has a shape obtained by substantially putting the bottom faces of cones against each other. Consequently, the dimension in the X-axis direction is also larger in the example illustrated in FIG. 5(A) where the interval between the PET detector 13a and the PET detector 13b is smaller.

When the effective field of vision of PET-MRI 26 illustrated in FIG. 5(B) is compared with the effective field of vision of PET-MRI 26 illustrated in FIG. 5(C), it is observed that, although the dimension along the axial direction of the bore (i.e., the Z-axis direction) does not change, the dimension in the Y-axis direction is smaller in the example illustrated in FIG. 5(C) where the interval between the PET detector 13a and the PET detector 13b is larger. Further, the dimension in the X-axis direction is also smaller in the example illustrated in FIG. 5(C) where the interval between the PET detector 13a and the PET detector 13b is larger.

As described above, the larger the interval between the PET detector 13a and the PET detector 13b is, the smaller is the effective field of vision of PET-MRI 26, and the higher is the possibility that the spatial resolution becomes degraded. On the contrary, if the interval between the PET detector 13a and the PET detector 13b is reduced, a problem may arise where PET and MRI interfere with each other. For example, a photomultiplier tube uses a mechanism in which electrons travel through the vacuum. Thus, when configured with photomultiplier tubes, the PET detectors 13a and 13b are more prone to be influenced by the magnetic field of MRI. Further, the scintillator is often configured with magnetic elements. Thus, the PET detectors 13a and 13b configured with such a scintillator may disturb homogeneity of the magnetic field. Such problems related to the interference between PET and MRI eventually leads to degraded image quality.

For these reasons, the PET-MRI apparatus 100 according to the present embodiment is configured to achieve a balance between the dimension of the effective field of vision 26 and the problem of interference between PET and MRI, by finding an appropriate overlapping relationship between the effective field of vision 26 and the PET image taking region and by making the interval between the PET detector 13a and the PET detector 13b as large as possible until the appropriate overlapping relationship is achieved, so as to avoid the problem of interference between PET and MRI. More specifically, on the basis of an MR image taken by performing a pre-scan, the PET-MRI apparatus 100 according to the present embodiment specifies positions of the PET detectors 13a and 13b in such a manner that the PET image taking region is included in the effective field of vision 26, and also, the difference between the image taking region and the effective field of vision 26 is kept small. The PET-MRI apparatus 100 then performs main scans implementing PET and MRI, after moving the PET detectors 13a and 13b to the specified positions.

The process described above is realized mainly by functional units included in the computer 10. As illustrated in FIG. 1, the computer 10 includes an MRI pre-scan unit 10a, a PET detector position specifying unit 10b, a PET detector moving controlling unit 10c, a shimming unit 10d, an MRI scan unit 10e, and a PET scan unit 10f. The computer 10 receives operations performed by an operator via the console 11. Further, the computer 10 causes a PET image, an MR image, and/or the like to be displayed on the display device 12.

The MRI pre-scan unit 10a is configured to perform an MRI pre-scan and to generate an MR image. In this situation, the pre-scan refers to a scan that is performed prior to another scan that follows (e.g., a scan performed to acquire a diagnosis image), in order to acquire data required by the scan that follows. For example, during the pre-scan, the MRI pre-scan unit 10a acquires an MR image used for determining the position of an image taking region of a diagnosis image, acquires data indicating a reception sensitivity distribution of the reception-purpose radio frequency coil 7, or acquires data used for adjusting homogeneity of intensities in the magnetostatic field.

For example, the MRI pre-scan unit 10a performs the pre-scan by controlling the sequence controller 16, the gradient coil driving circuit 4, the transmitting unit 6, the receiving unit 8, the MR data acquiring unit 9, and the like. Further, the MRI pre-scan unit 10a generates the MR image by reconstructing the MR data generated by the MR data acquiring unit 9. The MR image is used for determining the position of the image taking region of an MRI diagnosis image, as well as for a process performed by the PET detector position specifying unit 10b, as described below.

The PET detector position specifying unit 10b is configured to specify the positions of the PET detectors 13a and 13b, on the basis of the MR image taken by the MRI pre-scan unit 10a. For example, the PET detector position specifying unit 10b displays an "image taking region adjustment screen" on the display device 12, as a Graphical User Interface (GUI) used for adjusting the positions of the PET detectors 13a and 13b. The PET detector position specifying unit 10b then specifies the positions of the PET detectors 13a and 13b by receiving, on the displayed screen, an instruction (hereinafter, a "change instruction") to change either the positions of the PET detectors 13a and 13b or the effective field of vision 26. In addition, the PET detector position specifying unit 10b according to the present embodiment also specifies a position of the couchtop 2a on the basis of the MR image.

The PET detector moving controlling unit 10c is configured to control moving of the PET detectors 13a and 13b in accordance with the positions specified by the PET detector position specifying unit 10b. For example, by controlling the moving mechanisms 23, the PET detector moving controlling unit 10c controls the moving of the PET detectors 13a and 13b. In addition, the PET detector moving controlling unit 10c according to the present embodiment also controls moving of the couchtop 2a, in accordance with the position of the couchtop 2a specified by the PET detector position specifying unit 10b.

The shimming unit 10d is configured to adjust homogeneity of intensities in the magnetostatic field, in accordance with the positions of the PET detectors 13a and 13b. For example, at the time of the installation of the PET-MRI apparatus 100 or the like, the shimming unit 10d acquires, in advance, data (which reflects the influence of the magnetostatic field) used for correcting the homogeneity of the intensities in the magnetostatic field, while changing the interval between the PET detectors 13a and 13b that are provided so as to face each other while the magnetic-field center 20 is interposed therebetween. Further, on the basis of the data acquired in advance, the shimming unit 10d calculates a correction magnetic field that cancels out inhomogeneous components in the magnetostatic field. Further, in accordance with the calculated correction magnetic field, the shimming unit 10d specifies an electric current value (hereinafter, "current value") (i.e., a correction value). After that, the shimming unit 10d stores the positions of the PET detectors 13a and 13b and the current value into a storage unit (not shown), while keeping these pieces of information in correspondence with each other.

Further, when the MRI scan unit 10e performs a scan while the PET-MRI apparatus 100 is in operation, the shimming unit 10d obtains a current value that is kept in correspondence with the positions of the PET detectors 13a and 13b, from the storage unit. After that, the shimming unit 10d adjusts the homogeneity of the intensities in the magnetostatic field, by causing electric current having the obtained current value to flow through a correction coil (not shown) (i.e., by applying a correction magnetic field thereto). Further, together with this shimming process, the shimming unit 10d may also perform a conventional shimming process based on the data acquired during the pre-scan.

The MRI scan unit 10e is configured to perform an MRI scan after the PET detectors 13a and 13b have been moved, while the homogeneity in the magnetostatic field is being adjusted. For example, the MRI scan unit 10e performs the scan for acquiring a diagnosis image by controlling the sequence controller 16, the gradient coil driving circuit 4, the transmitting unit 6, the receiving unit 8, the MR data acquiring unit 9, and the like. Further, the MRI scan unit 10e generates an MR image by reconstructing the MR data generated by the MR data acquiring unit 9.

The PET scan unit 10f is configured to perform a PET scan after the PET detectors 13a and 13b have been moved. For example, the PET scan unit 10f performs the scan for acquiring a diagnosis image, by controlling the sequence controller 16, the PET detectors 13a and 13b, the PET detector power source 14, the PET data acquiring unit 15, and the like. Further, the PET scan unit 10f generates a PET image, by reconstructing the PET data generated by the PET data acquiring unit 15.

FIG. 6 is a flowchart of a processing procedure according to the present embodiment. As shown in FIG. 6, first, the MRI pre-scan unit 10a performs an MRI pre-scan and generates MR images used for determining positions (step S101). In this situation, the PET detectors 13a and 13b can be arranged in any arbitrary positions. For example, the PET detectors 13a and 13b may be positioned together on one side of the gantry, while being positioned away from the magnetic-field center 20. Alternatively, the PET detectors 13a and 13b may be positioned so as to have a large interval therebetween, while the magnetic-field center 20 is interposed therebetween.

Figure 7:
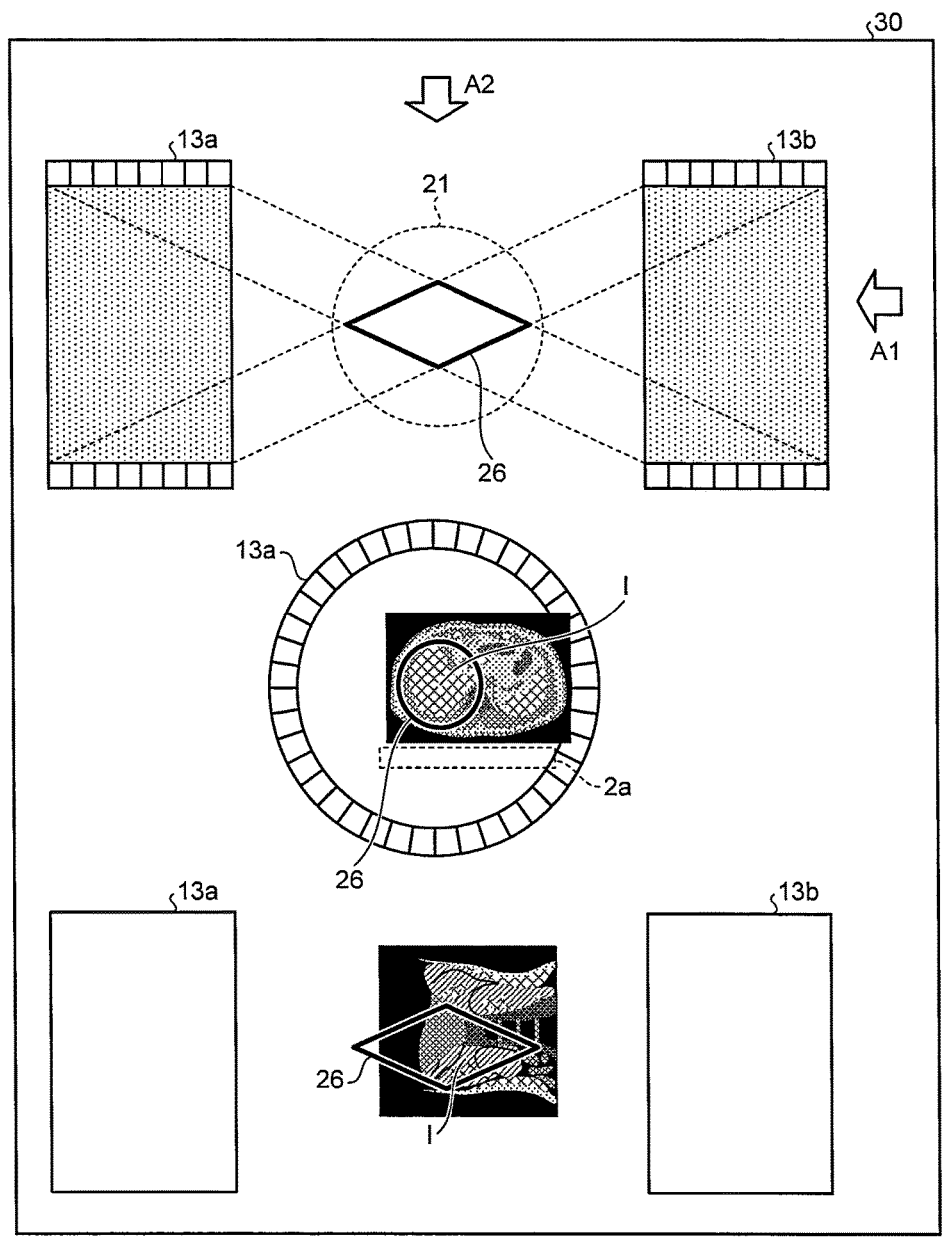
FIG. 7 is a drawing of an image taking region adjustment screen according to the present embodiment.
Figure 8:
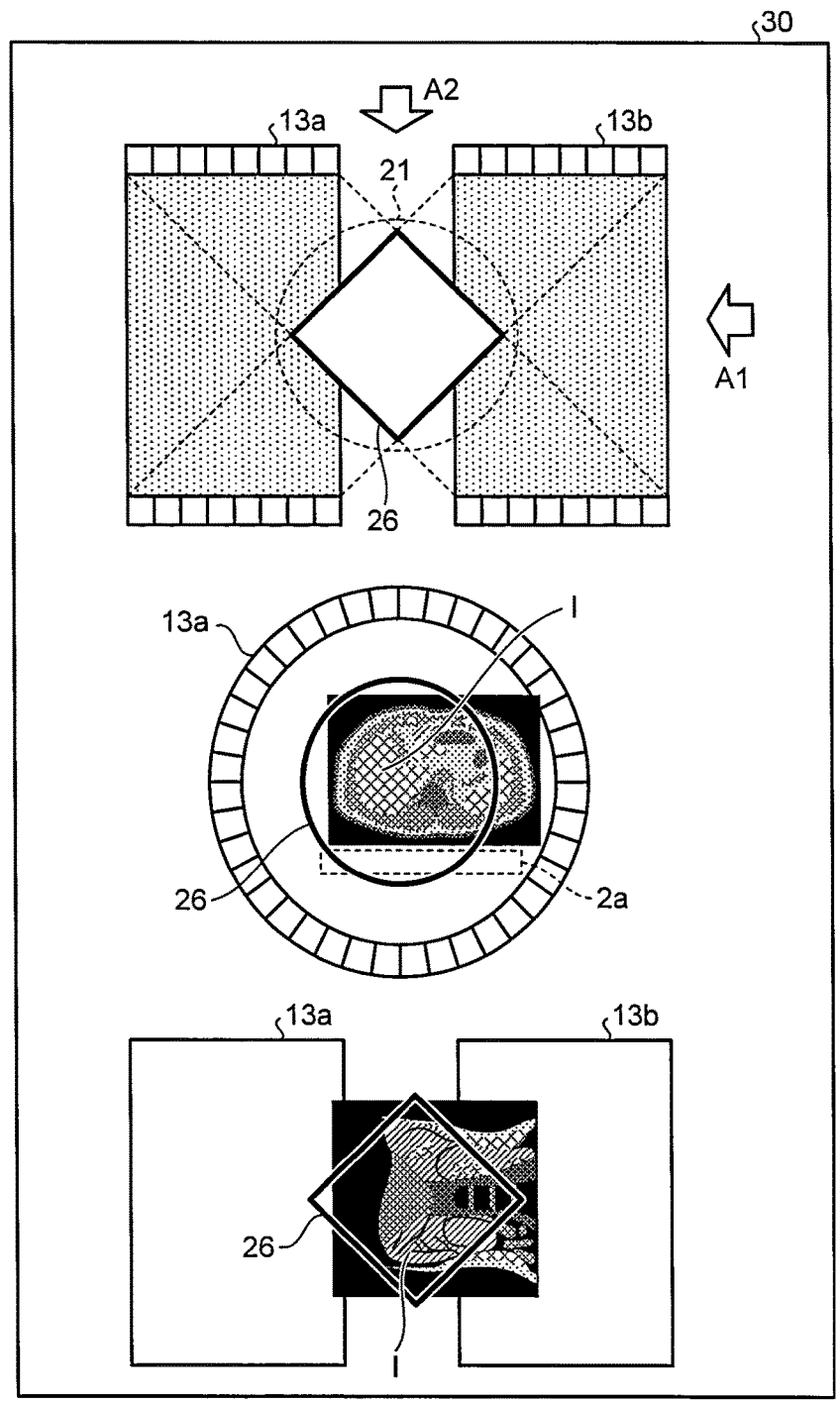
FIG. 8 is another drawing of the image taking region adjustment screen according to the present embodiment.
Figure 9:
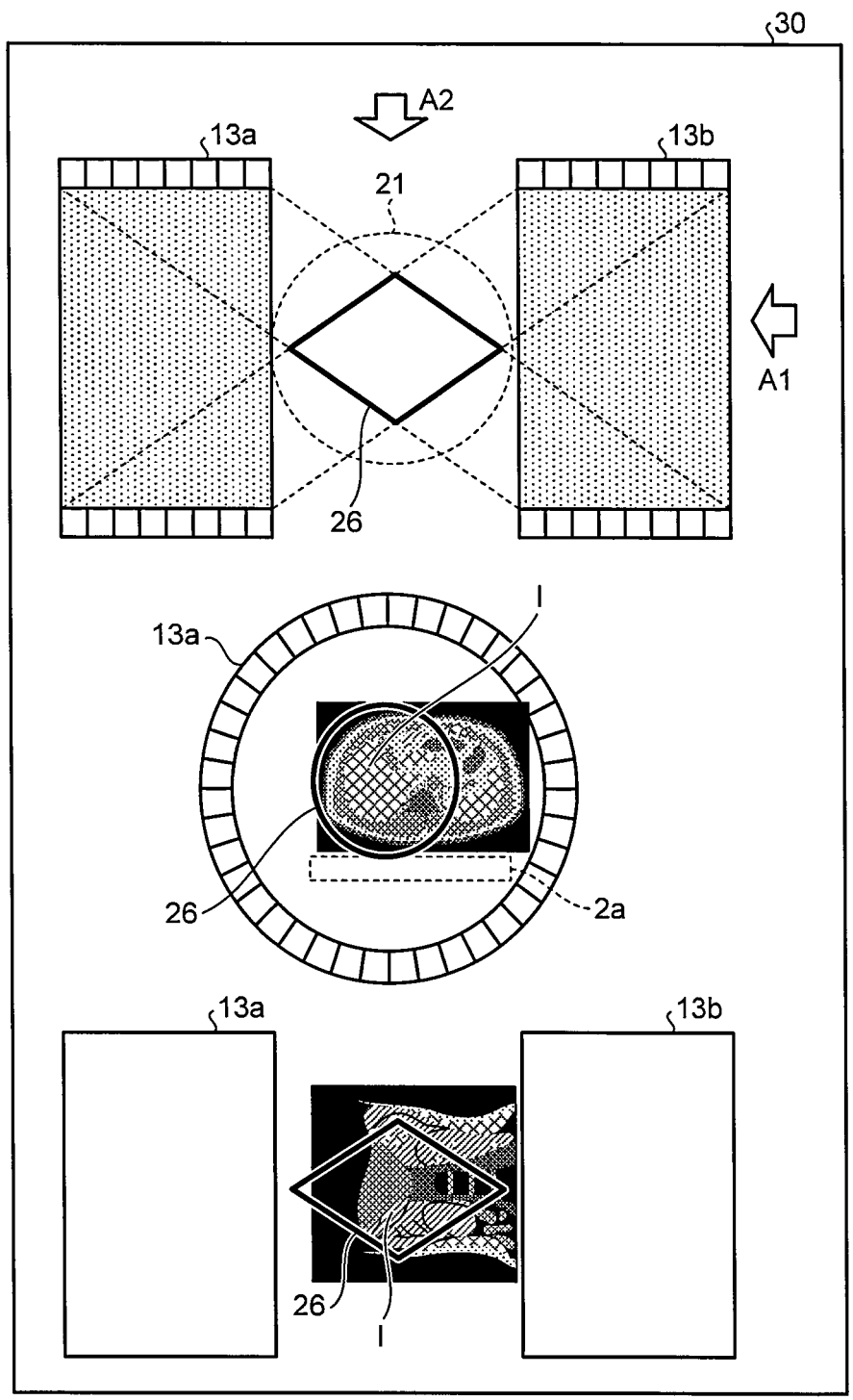
FIG. 9 is yet another drawing of the image taking region adjustment screen according to the present embodiment.

Subsequently, the PET detector position specifying unit 10b displays an image taking region adjustment screen on the display device 12 (step S102). FIGS. 7 to 9 are drawings of an image taking region adjustment screen 30 according to the present embodiment.

For example, as illustrated in FIG. 7, the PET detector position specifying unit 10b displays, as the image taking region adjustment screen, a schematic diagram in which it is possible to visualize a relationship between the positions of the PET detectors 13a and 13b and the effective field of vision of PET-MRI 26 (the upper section of FIG. 7).

In addition, for example, the PET detector position specifying unit 10b displays a schematic diagram in which an MR image (an axial image) taken on a body-axis cross-sectional plane and the effective field of vision of PET-MRI 26 are superimposed on a view of the PET detector 13a taken in the direction of an arrow A1 (the middle section of FIG. 7). Furthermore, for example, the PET detector position specifying unit 10b displays a schematic diagram in which an MR image (a coronal image) taken on a coronal cross-sectional plane and the effective field of vision of PET-MRI 26 are superimposed on a view of the PET detectors 13a and 13b taken in the direction of an arrow A2 (the lower section of FIG. 7). These MR images are the MR images that are used for determining the positions and were acquired and generated at step S101.

As described above, the PET detector position specifying unit 10b provides the operator with three-dimensional information, by displaying, in the superimposed manner, MR images corresponding to two directions, for example, from among the MR images used for determining the positions. Further, although omitted from FIG. 7, the PET detector position specifying unit 10b may further display an MR image (a sagittal image) taken on a sagittal cross-sectional plane so as to be superimposed on the schematic diagram shown in the upper section of FIG. 7. FIGS. 8 and 9 also illustrate the image taking region adjustment screen that is the same as the one shown in FIG. 7, but has a different interval between the PET detectors 13a and 13b from the one shown in FIG. 7.

In this situation, on the image taking region adjustment screen, the PET detector position specifying unit 10b according to the present embodiment receives a change instruction to change either the positions of the PET detectors 13a and 13b or the effective field of vision 26. For example, the operator is able to move the PET detector 13a to the right or to the left on the image taking region adjustment screen, by performing a drag-and-drop operation with a mouse. As a result, the PET detector position specifying unit 10b realizes a display in which the interval between the PET detectors 13a and the 13b is automatically reduced by moving the PET detector 13a to the right and moving the PET detector 13b to the left, as shown in FIG. 8, for example. In addition, as shown in the upper section of FIG. 8, the PET detector position specifying unit 10b displays the effective field of vision 26 on the image taking region adjustment screen after automatically changing the shape thereof to a larger rhomboid. Furthermore, as illustrated in the middle section and the lower section of FIG. 8, the PET detector position specifying unit 10b displays the effective field of vision 26 after changing the shape thereof in accordance with the direction thereof.

For example, let us discuss a situation where the operator looks at the image taking region adjustment screen shown in FIG. 7 and determines that the liver 1 serving as an image taking target is not completely included in the effective field of vision 26, especially in the coronal image taken on the coronal cross-sectional plane. In that situation, the operator reduces the interval between the PET detectors 13a and 13b on the image taking region adjustment screen. (Alternatively, the operator may enlarge the effective field of vision 26 so that the liver 1 is completely included in the effective field of vision 26). As a result, the PET detector position specifying unit 10b changes the image taking region adjustment screen to the one illustrated in FIG. 8, in response to the operation performed by the operator. In that situation, the operator once again looks at the image taking region adjustment screen illustrated in FIG. 8 and determines, at this time, that the effective field of vision 26 is too large in relation to the image taking region including the liver 1 serving as the image taking target, especially in the axial image taken on the body-axis cross-sectional plane. In that situation, the operator performs a fine-tuning process on the image taking region adjustment screen so as to enlarge the interval between the PET detectors 13a and 13b (Alternatively, the operator may perform a fine-tuning process so as to reduce the effective field of vision 26 so that the effective field of vision 26 becomes closer to the liver 1). As a result, the PET detector position specifying unit 10b changes the image taking region adjustment screen to the one illustrated in FIG. 9, in response to the operation performed by the operator.

As a result of the operator's repeating the fine-tuning process described above, as illustrated in FIG. 9, for example, the difference between the image taking region and the effective field of vision 26 becomes smaller, while the image taking region including the liver 1 is included in the effective field of vision 26. In another example, the operator may further operate the couchtop 2a so that, for instance, the center of the image taking target coincides with the center of the effective field of vision 26 in the schematic diagram shown in the middle section.

The image taking region adjustment screens illustrated in FIGS. 7 to 9 are merely examples, and possible embodiments are not limited to these examples. It is acceptable to modify the schematic diagrams and to add necessary information or eliminate information, as appropriate. For example, although FIG. 7 illustrates the three schematic diagrams in the upper, the middle, and the lower sections, it is acceptable to display only two of the three schematic diagrams. Further, the cross-sectional plane on which the MR image to be superimposed on any of the schematic diagrams is taken may be arbitrarily selected. Furthermore, it is also acceptable to display a body mark indicating the orientation of the patient P on the screen, so as to make it easier to understand the orientation of the patient P.

Returning to the description of FIG. 6, after having displayed the image taking region adjustment screen as described above, the PET detector position specifying unit 10b judges whether a change instruction has been received (step S103). After that, when the operator has completed a change instruction and has pressed a "confirm" button (not shown), for example, the PET detector position specifying unit 10b specifies the positions at this time as the positions of the PET detectors 13a and 13b and the couchtop 2a (step S104).

Subsequently, the PET detector moving controlling unit 10c controls moving of the PET detectors 13a and 13b and the couchtop 2a, in accordance with the positions specified by the PET detector position specifying unit 10b at step S104 (step S105).

Further, the shimming unit 10d adjusts homogeneity of the intensities in the magnetostatic field in accordance with the positions specified by the PET detector position specifying unit 10b at step S104 (step S106). More specifically, the shimming unit 10d adjusts the homogeneity of the intensities in the magnetostatic field by obtaining the current value kept in correspondence with the positions of the PET detectors 13a and 13b from the storage unit and causing electric power having the obtained current value to flow through the correction coil (not shown) (i.e., by applying an offset magnetic field thereto). After that, the MRI scan unit 10e and the PET scan unit 10f each perform a scan (step S107).

As described above, according to the present embodiment, on the basis of the MR images acquired during the pre-scan, the PET-MRI apparatus 100 finds the appropriate overlapping relationship between the effective field of vision 26 and the PET image taking region. Subsequently, the PET-MRI apparatus 100 takes the diagnosis-purpose images, after exercising control so as to move the PET detectors 13a and 13b and the couchtop 2a in the three-dimensional directions to such positions that achieve the appropriate overlapping relationship. Consequently, it is possible to improve the image quality.

OTHER EXEMPLARY EMBODIMENTS

Possible embodiments are not limited to the exemplary embodiments and the modification examples thereof described above.

In the embodiment described above, the method is explained in which the change instruction from the operator is received on the GUI. However, possible embodiments are not limited to this example. For example, it is acceptable to automatically specify the positions of the PET detectors 13a and 13b and the couchtop 2a, as a result of an image analysis process performed on an MR image. In that situation, for example, the PET detector position specifying unit 10b extracts the image taking target (e.g., the liver) by performing a publicly-known contour extracting process or the like on the MR image. Subsequently, the PET detector position specifying unit 10b specifies an optimal effective field of vision 26 in such a manner that the extracted image taking target is included in the effective field of vision 26, and also, the difference from the effective field of vision 26 is kept small. After that, the PET detector position specifying unit 10b specifies the positions of the PET detectors 13a and 13b and the couchtop 2a corresponding to the specified effective field of vision 26.

Further, in the embodiment described above, the example is explained in which the shimming unit 10d uses the current value specified in advance at the time of the installation of the PET-MRI apparatus 100 or the like for the shimming process; however, possible embodiments are not limited to this example. For instance, the shimming unit 10d may first move the PET detectors 13a and 13b and the couchtop 2a to appropriate positions and, at that point in time, the shimming unit 10d may acquire data reflecting the influence of the magnetostatic field and perform a shimming process by specifying a current value on the basis of the acquired data. In that situation, the MRI pre-scan unit 10a may omit the process to acquire the data reflecting the influence of the magnetostatic field.

For example, the shimming unit 10d specifies an image taking region to be used in a shimming image taking process, by using the MR image acquired at step S101. If the data reflecting the influence of the magnetostatic field includes data other than that of the image taking target, there is a possibility that it may not be possible to calculate an appropriate correction value. For example, it is often the case that the magnetostatic field distribution is significantly different between a heart region and a chest wall region. Thus, if the data other than that of the heart region is mixed in, there is a possibility that it may not be possible to make an appropriate adjustment due to an error occurring in the calculated correction value. For this reason, it is desirable to set the image taking region to be used in the shimming image taking process, while limiting the image taking region to the vicinity of the target organ.

Subsequently, the shimming unit 10d performs a shimming image taking process in the state resulting from the moving control exercised on the PET detectors 13a and 13b at step S105 and acquires the data reflecting the influence of the magnetostatic field. The data does not include any data other than that of the image taking target. The data also reflects the influence of the positions of the PET detectors 13a and 13b. Subsequently, the shimming unit 10d calculates a correction magnetic field (hereinafter, "performs a shimming calculation", as necessary) that cancels out inhomogeneous components in the magnetostatic field on the basis of the acquired data and specifies a current value (a correction value) in accordance with the calculated correction magnetic field. After that, the shimming unit 10d performs a shimming process by using the specified current value.

Next, the shimming process will be briefly explained. Generally speaking, shimming processes can roughly be divided into passive shimming processes and active shimming processes. A passive shimming process is to homogenize the magnetostatic field in an image taking region, by disposing shims or the like in an MRI gantry. More specifically, a plurality of spaces each of which extends in the z-axis direction (the axial direction of the bore) of the MRI gantry are circumferentially provided along the y direction, so that a shim tray is inserted into each of the spaces. Each of the shim trays has a plurality of shim pockets so that it is possible to adjust amounts and layouts of the shims in the z-axis direction. In contrast, an active shimming process is to homogenize the magnetostatic field in an image taking region by superimposing a correction magnetic field generated by a shim coil onto the magnetostatic field generated by the magnetostatic field magnet 1.

Inhomogeneity of a magnetostatic field can be expressed by dividing the components as follows: zeroth-order components $X_0$, $Y_0$, $Z_0$; first-order components $X_1$, $Y_1$, $Z_1$; and second-order components $X_2$, $Y_2$, $Z_2$, XY, ZY, ZX. There may be some other higher-order components such as third-order or higher components. An active shimming process is commonly performed for each of the inhomogeneous components. However, it is necessary to use shim coils that are in one-to-one correspondence with the corrected components. Thus, it is common practice to perform the correction process by narrowing down the target components, e.g., up to the first-order components or up to the second-order components. As described above, during the shimming calculation process, the signal acquiring process for measuring the magnetic field distribution in the region of interest is actually performed, so that a magnetic field distribution is expanded for each of the magnetic field components serving as shimmed targets and so that the correction magnetic field that cancels out the inhomogeneous components in the magnetostatic field is obtained. After that, the current value (i.e., the correction value) to be supplied to each of the shim coils in order to generate the correction magnetic field is calculated.

The explanation above states that the shimming unit 10d first moves the PET detectors 13a and 13b and the couchtop 2a to the appropriate positions, and at that point in time, the shimming unit 10d may acquire the data reflecting the influence of the magnetostatic field and perform the shimming process by specifying the current value on the basis of the acquired data. This means that, instead of performing an active shimming process at the time of the installation of the PET-MRI apparatus 100, an active shimming process is performed at the stage where the PET detectors 13a and 13b and the couchtop 2a have been moved to the appropriate positions. In that situation, a passive shimming setting (a layout and an amount of shims) can be determined at the time of the installation, for example, in such a manner that the correction made by the active shimming process is small in a typical layout or in a plurality of layouts with which the PET-MRI apparatus 100 is actually used in a clinical environment. These layouts include not only layouts in which the PET detectors 13a and 13b are installed in the MRI gantry, but also layouts in which the PET detectors 13a and 13b are not installed in the MRI gantry.

Further, in the embodiment described above, the method is explained by which the positions of the PET detectors 13a and 13b are specified on the basis of the MR images; however, possible embodiments are not limited to this example. For example, it is also acceptable to specify the positions of the PET detectors 13a and 13b on the basis of an image taking condition set with regard to the MRI image taking process. In other words, the PET detector position specifying unit 10b may specify the positions of the PET detectors 13a and 13b, on the basis of the image taking condition that is set with regard to the MRI image taking process.

This process will be explained with a specific example. To perform an MRI image taking process, various types of image taking conditions are set before the image taking process. For example, the PET-MRI apparatus 100 receives, as the image taking conditions, a Field of View (FOV) in the Phase Encode (PE) direction, an FOV in the Read Out (RO) direction, a thickness of each slice, a quantity of slices, and the like. For example, if the image taking target is the heart, the PET-MRI apparatus 100 receives a setting with 25 cm×25 cm as an FOV, 4 mm as a thickness of each slice, and 20 as a quantity of slices, for instance. In that situation, on the basis of these image taking conditions received as the setting, the PET-MRI apparatus 100 uses, as an image taking region, a region that is centered on the magnetic-field center 20 and corresponds to the setting of 25 cm×25 cm as the FOV, 4 mm as the thickness of each slice, and 20 as the quantity of slices and specifies an optimal effective field of vision 26 in such a manner that the image taking region is included in the effective field of vision 26, and also, the difference from the effective field of vision 26 is kept small.

Further, the configuration of the PET-MRI apparatus is not limited to the example described above. For example, it is acceptable to use PET detectors in a double-ring form as the PET detectors. Further, in other examples, the PET detectors may be provided on the inside of the bore or may be provided as being separated into a gantry side section and a couchtop side section.

Further, the exemplary embodiments described above are explained on the assumption that the PET-MRI apparatus is the medical image diagnosis apparatus in which a PET apparatus is used in combination; however, possible embodiments are not limited to this example. The exemplary embodiments described above may similarly be applied to a PET-CT apparatus, for example. In that situation, for instance, the PET-CT apparatus includes a CT pre-scan unit, in place of the MRI pre-scan unit 10a. Further, the PET-CT apparatus includes a CT scan unit, in place of the MRI scan unit 10e. In addition, the PET-CT apparatus includes other functional units of a CT apparatus, in place of the functional units in the exemplary embodiments described above on the assumption that the MRI apparatus is used. In that situation, the PET detector position specifying unit 10b described above specifies the positions of the PET detectors 13a and 13b on the basis of a CT image taken by performing a pre-scan.

Examples of the pre-scan to take the CT image include a pre-scan to acquire a scanogram. The pre-scan may be, for example, a helical scan that is performed at a high speed while using a tube current lower than that of a main scan and a helical pitch longer than that of the main scan. From the data acquired during the pre-scan, the CT pre-scan unit generates, for example, a scanogram of a front image obtained when an X-ray tube is positioned at 0° and a scanogram of a lateral image obtained when the X-ray tube is positioned at 90°. The PET detector position specifying unit 10b then displays, as the image taking region adjustment screen described above, a schematic diagram in which, for example, these two scanograms are displayed together with an effective field of vision of PET-CT, in a superimposed manner.

In the exemplary embodiments described above, the example is explained in which the positions of the PET detectors 13a and 13b and the couchtop 2a are specified on the basis of the various types of image taking conditions set for the MRI image taking process. Similarly, the PET-CT apparatus may specify the positions of the PET detectors 13a and 13b and the couchtop 2a, on the basis of various types of image taking conditions such as an FOV, a thickness of each slice, and a quantity of slices, and the like.

By using the medical image diagnosis apparatus and the PET-MRI apparatus according to at least one aspect of the embodiments described above, it is possible to improve the image quality.

While certain embodiments of the present invention have been described, these embodiments have been presented by way of examples only, and are not intended to limit the scope of the inventions. These exemplary embodiments may be embodied in a variety of other forms; furthermore, various omissions, substitutions, and changes may be made without departing from the spirit of the inventions. The inventions defined in the accompanying claims and their equivalents are intended to cover various embodiments and modifications, in the same manner as those embodiments and modifications would fall within the scope and spirit of the inventions.

What is claimed is:

1. A medical image diagnosis apparatus, comprising:
   a first imaging apparatus configured to perform a first image taking process by implementing Positron Emission Tomography (PET) while using a first PET detector and a second PET detector, each PET detector being configured to detect annihilation radiation emitted from a positron emission nuclide and being provided so that an interval therebetween is adjustable;
   a second imaging apparatus configured to perform a second image taking process different from that of the first imaging apparatus; and
   processing circuitry configured to
      cause the first imaging apparatus and the second imaging apparatus to perform the first and second image taking processes, respectively,
      specify positions of the first PET detector and the second PET detector, based on a medical image taken by the second imaging apparatus,
      control moving of the first PET detector and the second PET detector in accordance with the specified positions, and
      cause the first imaging apparatus and the second imaging apparatus to again perform the first and second image taking processes, respectively, after the first PET detector and the second PET detector have been moved.

2. The medical image diagnosis apparatus according to claim 1, wherein the processing circuitry is further configured to specify, within the medical image, an image taking region that includes an image taking target site, and specify the positions of the first PET detector and the second PET detector based on the specified image taking region.

3. The medical image diagnosis apparatus according to claim 2, wherein the processing circuitry is further configured to specify, within the medical image, the image taking region that includes the image taking target site, and specify the positions of the first PET detector and the second PET detector so that the specified image taking region is included in an effective field of vision that is for PET image taking processes and is formed by the first PET detector and the second PET detector.

4. The medical image diagnosis apparatus according to claim 3, wherein the processing circuitry is further configured to
   cause a display to display a screen that shows, in a superimposed manner, the medical image and the effective field of vision formed by the first PET detector and the second PET detector,
   receive a change instruction to change either the positions of the first PET detector and the second PET detector or the effective field of vision, and show the effective field of vision, which changes in accordance with the positions, and
   specify the positions of the first PET detector and the second PET detector by receiving the change instruction on the screen.

5. The medical image diagnosis apparatus according to claim 4, wherein the processing circuitry is further configured to cause the display to display, as the screen, a schematic diagram in which it is possible to visualize a relationship between the positions of the first PET detector and the second PET detector and the effective field of vision.

6. The medical image diagnosis apparatus according to claim 4, wherein the processing circuitry is further configured to cause the display to display, on the screen, medical images corresponding to at least two directions.

7. The medical image diagnosis apparatus according to claim 3, wherein the processing circuitry is further configured to
   perform an image analysis process on the medical image and extract the image taking target site from the medical image, and
   specify the positions of the first PET detector and the second PET detector so that the extracted image taking site is included in the effective field of vision that is for PET image taking processes and is formed by the first PET detector and the second PET detector.

8. The medical image diagnosis apparatus according to claim 1, wherein the medical image taken by the second imaging apparatus is a medical image taken during a pre-scan performed by the second imaging apparatus.

9. The medical image diagnosis apparatus according to claim 1, wherein the processing circuitry is further configured to specify a position of a couchtop of a couch, based on the medical image, and control moving of the couchtop, in accordance with the specified position of the couchtop.

10. The medical image diagnosis apparatus according to claim 1, wherein the second imaging apparatus includes a Magnetic Resonance Imaging (MRI) device to perform MRI as the second image taking process, the medical image diagnosis apparatus is a PET-MRI apparatus and the processing circuitry is further configured to adjust homogeneity of intensities in a magnetostatic field in accordance with the positions of the first PET detector and the second PET detector, and the first imaging apparatus and the second imaging apparatus perform the first and second image taking processes, respectively, by implementing PET and MRI, while the homogeneity of the intensities in the magnetostatic field is being adjusted.

11. The medical image diagnosis apparatus according to claim 10, wherein processing circuitry is further configured to store in advance, positions of the first PET detector and the second PET detector in correspondence with electric current values used for correcting the magnetostatic field, and adjust the homogeneity of the intensities in the magnetostatic field by using one of the electric current values that is kept in correspondence with the specified positions.

12. The medical image diagnosis apparatus according to claim 1, wherein the second imaging apparatus includes a Computed Tomography (CT) device to perform CT as the second image taking process.

13. A PET-MRI apparatus, comprising:

a first imaging apparatus configured to perform a first image taking process by implementing PET while using a first PET detector and a second PET detector, each PET detector being configured to detect annihilation radiation emitted from a positron emission nuclide and being provided so that an interval therebetween is adjustable;

a second imaging apparatus including a Magnetic Resonance Imaging (MRI) device to perform MRI as a second image taking process; and processing circuitry configured to cause the first imaging apparatus and the second imaging apparatus to perform pre-scans by implementing PET and MRI, respectively, specify positions of the first PET detector and the second PET detector, based on an MR image taken during the pre-scan performed by the second imaging apparatus, control moving of the first PET detector and the second PET detector in accordance with the specified positions, and cause the first imaging apparatus and the second imaging apparatus to perform main scans by implementing PET and MRI, respectively, after the first PET detector and the second PET detector have been moved.

14. A medical image diagnosis apparatus, comprising:

a first imaging apparatus configured to perform a first image taking process by implementing PET while using a first PET detector and a second PET detector, each PET detector configured to detect annihilation radiation emitted from a positron emission nuclide and being provided so that an interval therebetween is adjustable;

a second imaging apparatus configured to perform a second image taking process different from that of the first imaging apparatus; and processing circuitry configured to cause the first imaging apparatus and the second imaging apparatus to perform the first and second image taking processes, respectively, specify positions of the first PET detector and the second PET detector, based on an image taking condition set with regard to the second image taking process performed by the second imaging apparatus, control moving of the first PET detector and the second PET detector in accordance with the specified positions, and cause the first imaging apparatus and the second imaging apparatus to again perform the first and second image taking processes, respectively, after the first PET detector and the second PET detector have been moved.

15. The medical image diagnosis apparatus according to claim 14, wherein the second imaging apparatus includes a Magnetic Resonance Imaging (MRI) device to perform MRI as the second image taking process.

16. The medical image diagnosis apparatus according to claim 14, wherein the second imaging apparatus includes a Computed Tomography (CT) device to perform CT as the second image taking process.

* * * * *